US005653734A

United States Patent [19]
Alt

[11] Patent Number: 5,653,734
[45] Date of Patent: Aug. 5, 1997

[54] METHOD OF ATRIAL DEFIBRILLATION EMPLOYING A TEMPORARY IMPLANTED CATHETER

[76] Inventor: Eckhard Alt, Eichendorffstrasse 52, Ottobrunn, Germany, 85521

[21] Appl. No.: 630,907

[22] Filed: Apr. 4, 1996

Related U.S. Application Data

[62] Division of Ser. No. 222,242, Apr. 4, 1994, Pat. No. 5,571,159.

[51] Int. Cl.$^6$ .................................................. A61N 1/39
[52] U.S. Cl. ........................................................... 607/5
[58] Field of Search ............................... 607/5, 116, 122, 607/125, 127, 128

[56] References Cited

U.S. PATENT DOCUMENTS

| | | | |
|---|---|---|---|
| 3,995,623 | 12/1976 | Blake et al. | 128/2.06 E |
| 5,000,190 | 3/1991 | Petre | 128/713 |
| 5,304,139 | 4/1994 | Adams et al. | 607/122 |
| 5,403,351 | 4/1995 | Saksena | 607/4 |
| 5,433,729 | 7/1995 | Adams et al. | 607/5 |

Primary Examiner—William E. Kamm
Attorney, Agent, or Firm—Wigman, Cohen, Leitner & Myers, P.C.

[57] ABSTRACT

Atrial fibrillation disorders are treated by locating low impedance electrodes positioned on a single catheter body passing through the pulmonary artery valve to locate the electrodes respectively in the right atrium and the pulmonary artery. Thus an electrical energy impulse of the order of three joules is passed through a heart and tissue path establishing a field gradient for resetting atrially fibrillating cells to convert atrial fibrillation into sinus rhythm. A special non-implantable catheter for temporary use provided for this treatment method is characterized by an inflatable balloon on the distal tip end, two low impedance energy discharging electrodes spaced to reside respectively in the right atrium and the pulmonary artery and a flexible polymer catheter body sheath of a diameter of the order of two millimeters. Inflating and deflating of the distal balloon facilitates the positioning of the catheter and guarantees a stable position during the application of the electrical energy shock for conversion of atrial fibrillation.

12 Claims, 2 Drawing Sheets

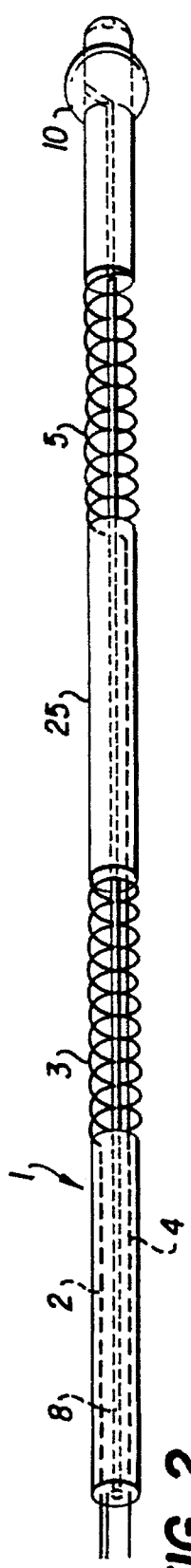
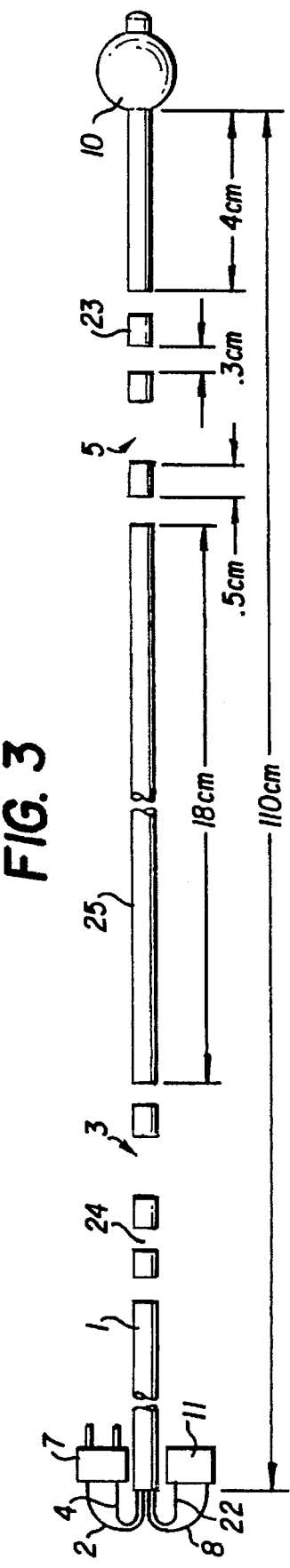
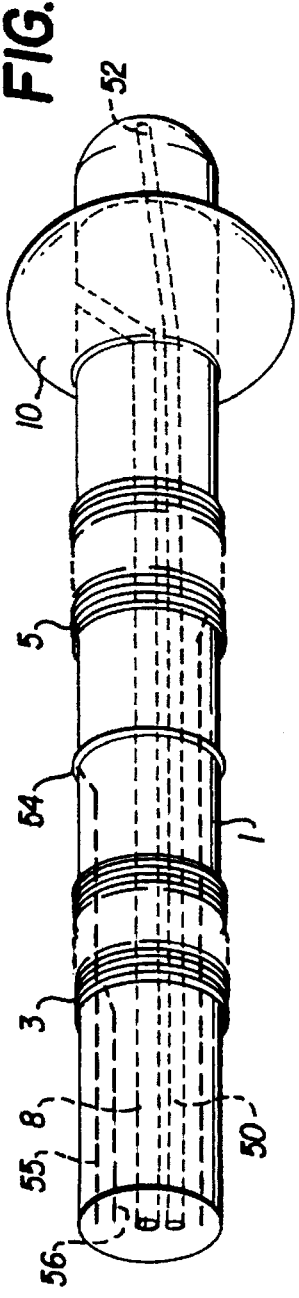
FIG. 2
FIG. 3
FIG. 4

METHOD OF ATRIAL DEFIBRILLATION EMPLOYING A TEMPORARY IMPLANTED CATHETER

This application is a division of application Ser. No. 08/222,242 filed 4 Apr. 1994 and now U.S. Pat. No. 5,571,159.

TECHNICAL FIELD

This invention relates to the treatment of atrial fibrillation, as distinguished from ventricular fibrillation, and special catheter for discharge of electrical energy therefor in the region of the heart to convert atrial fibrillation into sinus rhythm, and more particularly it relates to temporary monitoring and treatment of atrial arrhythmic disorders with non-implantable catheters threaded into the heart.

BACKGROUND ART

With current trends toward longer life expectancy the occurrence of atrial fibrillation increases significantly in all industrial nations. Currently atrial fibrillation is the main cause for hospitalization in the U.S.A. for arrhythmic disorders. It is also the most underlying reason for cerebrovascular stroke events. A solution to atrial fibrillation diseases are favored to correct its complication upon life and increase life expectancy, and also hemodynamics and thromboembolic complications favor a solution to such diseases by converting atrial fibrillation into sinus rhythm. However the use of antiarrhythmic drugs effective to preserve sinus rhythm produce a significant risk of proarrhythmias and reduced survival rate.

Also external shock with energies between 100 and 350 joules is a standard therapy for converting atrial fibrillation into sinus rhythm. The risks and complications of this type of therapy include late ventricular fibrillation, pericarditis due to the high electrical current and fractures of the spine and ribs following muscular contractions with high energy shock application.

The art of implanted atrial defibrillation electrodes using lower energies is well developed, as disclosed for example by J. Adams, et al. in U.S. Pat. No. 5,282,837, Feb. 1, 1994 for Atrial Defibrillator and Method. Therein, defibrillating energy is released from an implanted defibrillator for discharge between two electrodes of an implanted catheter threaded through the coronary sinus with energy discharge electrodes respectively located in positions beneath the left atrium near the left ventricle and in a region adjacent the right atrium coronary sinus ostium for minimizing ventricular fibrillation potential. The implanted defibrillator senses arrythmia and controls the energy discharge.

Ventricular fibrillation is also arrested with implanted systems as disclosed by T. Shulte, et al. in U.S. Pat. No. 5,269,319 by means of two defibrillation electrodes on a single catheter inserted via the superior vena cava into the right atrium and right ventricular cavity respectively. This system discloses the manner in which the defibrillation impulse energy is synchronized with the R-waves and provides for detection of the R-waves for that purpose.

It is a general object of this invention to provide improved treatment of atrial fibrillation on a temporary basis and correct the foregoing deficiencies of the prior art.

A further objective of this invention is to significantly reduce the amount of energy required for treatment of atrial fibrillation from external impulse generators with a hybrid system of internal defibrillating electrodes powered by external energy and control means.

However there are problems related to prior art electrodes both in the necessity to implant and the requirement to process enough energy for defibrillation in circumstances. In particular the effort that it takes to install and operate implanted systems is not tolerable when life atrial fibrillation occurs only rarely. The nature of effective prior art electrodes is generally intrusive with large electrode areas necessary to handle the high energy impulses that can initiate rejection reactions in the human body. Also implantation of netting, barbs and anchors in the region of the heart is not tolerable and not feasible for only temporary systems.

There are such conditions as congestive heart failure which after defibrillation can require continuous monitoring rather than isolated shock treatment. Furthermore cardiac surgical conditions that need post-operative monitoring for atrial dysrhythmias and defibrillation, require instantaneous treatment when atrial fibrillation is detected.

Accordingly it is a further object of this invention to provide a method and accompanying instrumentation for temporary use for limited periods of time to continuously monitor and instantaneously to treat dysrhythmias and atrial fibrillation with adequate electric field gradient shock energy, without implantation.

Other objects, features and advantages of the invention will be found throughout the following description, the accompanying drawings and the claims.

DISCLOSURE OF THE INVENTION

This invention answers the need for temporary but on line monitoring and treatment of atrial arrythmia by defibrillation. Such methods of treatment and associated improved catheter equipment can be used to reduce risks of complications from conventional shock conversion of atrial fibrillation into sinus rhythm. Thus dysrhythmias, congestive heart failure and post-operative problems after cardiac surgery can be treated with little delay and reduced risk incurred than with conventional methods.

In the method of treating atrial fibrillation disorders in accordance with this invention two low impedance electrodes positioned on a single catheter body are passed through the right atrium and pulmonary artery valve with one resident in the right atrium and the other resident in the pulmonary artery. This permits the discharge of electrical impulse energy of the order of three to seven joules from the electrodes to pass through the intervening heart blood and tissue path to establish a field gradient of sufficient amplitude for resetting atrially fibrillating cells and thereby converting atrial fibrillation into sinus rhythm. The patient is monitored continuously during high risk periods of time by external control and impulse generating equipment coupled to the internal catheter for instantaneous use under prescribed conditions.

This procedure is accomplished with a non-implantable atrial defibrillation catheter specially constructed for threading through the right ventricle and the pulmonary valve of the heart into the pulmonary artery to dispose temporarily two low impedance electrical impulse energy discharge electrodes respectively in the pulmonary artery and right atrium. The electrodes thereby encompass an area that permits reset of virtually all atrially fibrillating cells in the presence of a shock impulse that creates an adequate strength electric field gradient.

A distal tip end of said catheter carries an inflatable balloon connected by a lumen to a proximal end of the catheter for external control of inflation. This balloon serves two unique purposes, namely (1) when partly inflated it is a propellant agent acting as a vehicle with a sail for carrying the catheter tip with the flow of blood through the right ventricle and the pulmonary artery valve into the pulmonary artery, and (2) when fully inflated it serves as a temporary anchor in the pulmonary artery so that the portion of the catheter towards the proximal end that will reside in the heart and atrium can be shaped for its temporary resident position by forces exerted from the proximal end external to the body. When installed the balloon may be deflated to produce only nominal impediment to flow of blood in the pulmonary artery.

On the catheter, one of two low impedance energy dispersing defibrillation electrodes is disposed near the distal tip end of the catheter. The other defibrillation electrode is separated by a length of electrically insulating catheter sheath material of the order of twenty centimeters in length. Thereby the proximal defibrillation electrode is lodged in the right atrium when the distal defibrillation electrode is lodged in the pulmonary artery. In this position, the intervening electrically insulating catheter sheath passes through the pulmonary artery valve and lodges therein. To avoid interference with the functioning of the artery valve the catheter structure along the length of the insulating material separating the two defibrillation electrodes constitutes a flexible polymer sheath of a diameter in the order of two millimeters encompassing preferably a single flexible electrical lead connected from the distal defibrillation electrode to lead from the proximal end of the catheter. Also encompassed is an internal lumen leading to the distal end balloon for taking blood samples, for injection of fluids and for monitoring of the pulmonary artery pressure and of the pulmonary artery wedge pressure. This catheter structure permits the pulmonary artery valve to function for reasonable periods of time substantially normally in the presence of the catheter. An additional third ring electrode on the catheter situated in a position to detect the intracardiac ECG serves as sensing and pacing electrode for triggering of the defibrillation shock wave for pacing the heart.

Other objects, features and advantages of the invention are set forth throughout the following description, claims and the appended drawings.

BRIEF DESCRIPTION OF THE DRAWINGS

In the accompanying drawings, wherein like reference characters are used to facilitate comparison of similar features in the various views, FIG. 2 is a diagrammatic, foreshortened sketch of the distal end region of the atrial defibrillation catheter structure afforded by this invention, FIG. 3 is a foreshortened sketch dimensionally setting forth detailed structure of one preferred embodiment of the atrial defibrillation catheter, FIG. 4 is a modified catheter with a lumen for continuous monitoring and infusion of fluids into the body, such as required in post-operative procedure.

THE PREFERRED EMBODIMENT

Figure 1:
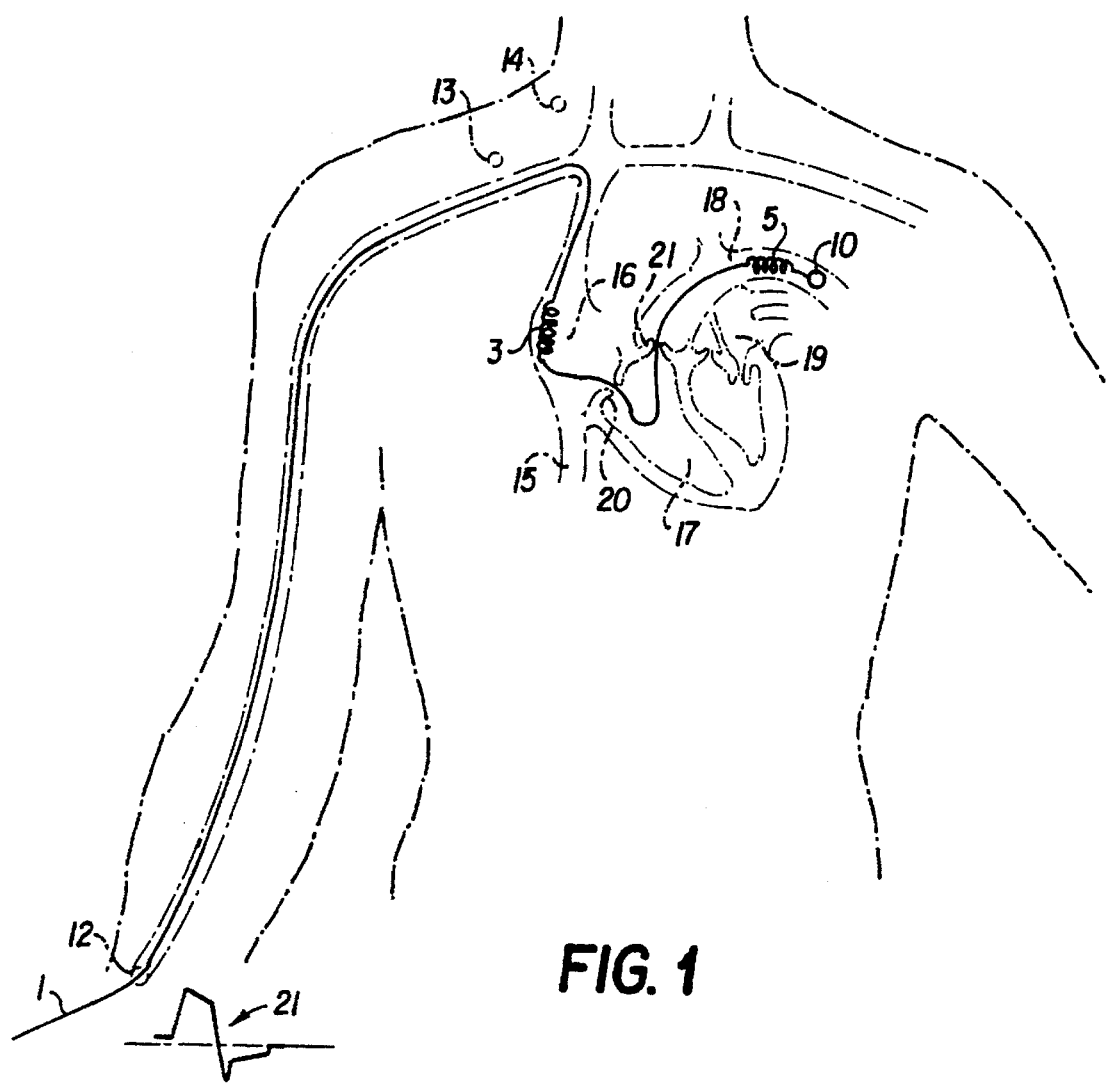
FIG. 1 is a schematic sketch of the atrial defibrillation catheter lodged in place within the heart for defibrillation in accordance with the method of this invention.
Figure 5:
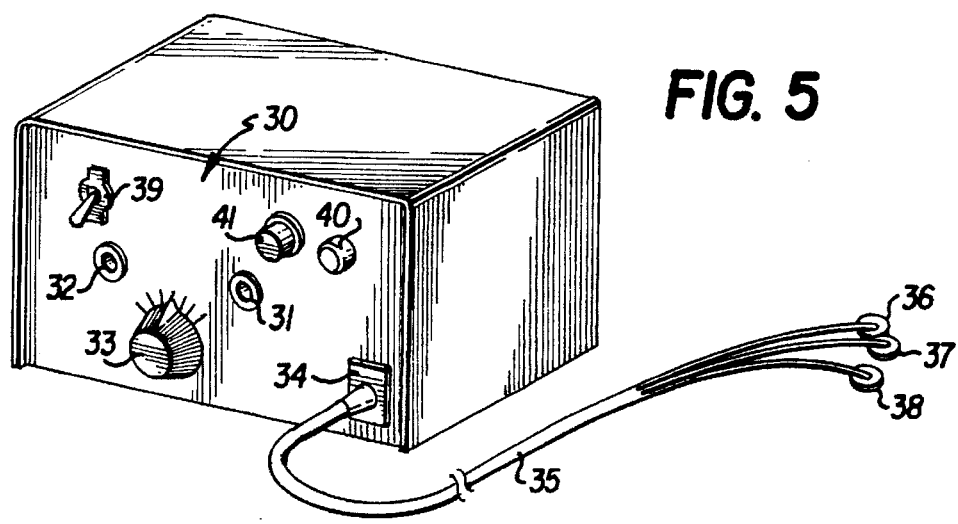
FIG. 5 is a block sketch of the external control center for defibrillation in accordance with the method introduced by this invention.

The sketch of the human body in FIG. 1 shows a single catheter 1, inserted at the preferable brachial vein puncture site 12 in the right arm to pass through the right atrium 16 into the heart. Internally embedded conductors 2 and 4, better seen in FIGS. 2 and 3, terminate at the proximal end in an external electrical connector 7 which in turn provides electrical energy from the external atrial defibrillator energy source and control system 30 (FIG. 5). These conductors 2 and 4 terminate at the distal end in the defibrillation electrodes 3 and 5 which are lodged respectively in the right atrium 16 and the pulmonary artery 18.

The catheter is constructed of a polymer sheath flexible enough to pass through the venous system of the human body and to attain the configuration shown in the heart. A typical diameter is two millimeters. The electrical conductors 2, 4 are flexible stranded wires for carrying enough impulse defibrillation energy to the respective defibrillation electrodes 3, 5 for defibrillation, typically in the order of about three to seven joules in accordance with this invention.

The structure of electrodes 3 and 5 is critical for defibrillation and thus requires a significant electrode surface exposure area to heart blood and tissue for transmitting the necessary shock impulse energy, preferably the shape of biphasic impulse 21. To produce the required surface area and to locate the electrodes in the respective atrium and pulmonary artery locations necessary for establishing the electric field path through the heart for atrial defibrillation, the electrodes are preferably constructed in the manner and with dimensions such as shown in FIG. 3.

The overall length of catheter 1 therefore is 110 cm from distal end to proximal end, and the outside diameter is about two mm. The inflatable balloon 10 resides at the distal end tip and is inflated by, way of an encompassed lumen 8 which extends from the catheter proximal end to a plug 11 that provides air control for inflation and deflation of the balloon, etc. by connection to an external syringe of 2 cc. Also for monitoring, for taking blood samples and infusion of body fluids, particularly critical at the post-operative stage, a further lumen 22 is provided to terminate at or near the distal end.

Each of the defibrillation electrodes 3, 5 is constructed of a series of 0.5 cm long rings 23, typically nine, separated by 0.2 cm spacings 24. The distal electrode 5 is spaced about four cm from the balloon, and the two electrodes 3, 5 have an insulating sheath spacer 25 eighteen cm. long between them. The stainless steel rings 23 and interim spacings 24, which constitute insulating catheter sheath polymer material provide a smooth surface which does not irritate human tissue when passed through the venous system. The area and length of the rings therefore is sufficient to create an electric field gradient of adequate strength through the heart to reset substantially all atrially fibrillating cells and establish sinus rhythm with short duration shock impulse energy of an average of three joules, as confirmed by a study conducted by the applicant in patients with atrial fibrillation following an enlarged and diseased atrium.

The very flexible spacer sheath 25 between the electrodes requires only one electrical wire and is smooth and small diameter so that its position through the pulmonary artery valve 21 for reasonable periods of time will not adversely affect its functioning. Nor will this spacer affect the function of the tricuspid valve 20. Thus the catheter may be used in place for several days in a post-operative stage for monitoring and defibrillating in the event an atrial fibrillation is detected. Furthermore the flexible sheath polymer spacers 24 between the stainless steel rings 23 afford enough flexibility at the electrode sites to bend the catheter about body cavities during insertion and positioning in the heart. Other types of electrodes such as braided metal mesh serves as well for the purpose of shocking electrodes 3 and 5.

In the insertion of the catheter, the balloon 10 is inflated partly in order to facilitate the positioning of the defibrillation catheter 1 into the pulmonary artery 18. The inflation of the balloon in the right atrium 16 will help advance the catheter with the blood flow into the pulmonary artery 18. The inflated balloon 10 also helps maintain a stable position of the distal end of the catheter 1 in the pulmonary artery, for example, temporarily as the catheter 1 is fed into the heart to attain the position shown passing from the right ventricle 17 into the left pulmonary artery 18. The fixation of the distal tip serves additionally the aim of advancing the catheter 1 to manipulate the shocking electrode 3 into contact with the atrium 16 for good electrical contact when the defibrillation pulse is applied without dislodging the electrode 5 from its position in the pulmonary artery. Furthermore, inflation and deflation of the balloon 10 enables measurements of pulmonary wedge pressures.

The catheter 1 may alternatively be inserted at the subclavian puncture site 13 or the internal jugular site 14. Also, it would be possible to approach through the femoral vein and the inferior vena cava 15. In any event the catheter passes through the right atrium 16 to lodge the defibrillator electrode 3 therein, and extends through the right ventricle 17 and the pulmonary artery valve 21 into left pulmonary artery 18 to lodge the defibrillator electrode 5 in the pulmonary artery 18. This critical positioning permits a vector of electric energy to pass through the left atrium 18.

The external atrial defibrillator 30 is shown in FIG. 5. It provides an electric shock impulse, preferably biphasic (21) of variable duration, preferably four milliseconds, with a second pulse of opposite polarity of two and one half milliseconds. Also it provides variable energy, as indicated by knob 33 in a range between one and ten joules. Plugs 31 and 32 permit the anode and cathode leads 2, 4 of the catheter 1 to be connected. For triggering the defibrillation shock pulse synchronously with the R-wave, the ECG lead 35 with surface electrodes 36, 37, 38 is provided. The external defibrillator 30 is turned on and off with switch 39. A temporary mode indicating correct synchronization with the R-wave is indicated by the LED 40 when the momentary switch 41 is depressed for testing without generating shock pulses. Other controls may include atrial fibrillation detectors that can be coupled to automatically generate a shock wave under prescribed conditions, and fluid controls for lumens 8 and 22 to monitor internal body fluids and provide for balloon inflation.

In FIG. 2, a foreshortened schematic sketch of the distal end of a catheter 1 provided in accordance with this invention shows the defibrillation electrodes 3, 5 separated by the intermediate separating catheter sheath section at the distal end. The balloon 10 is positioned at the distal end tip of the catheter 1. The internal lumen 8 operates the balloon, and may as shown in FIG. 4 be accompanied by the additional lumen 50 that terminates at the distal end tip 52. The additional electrode ring 54 intermediate electrodes 3 and 5 together with conductor wire 55 is used for pacing and sensing of intrinsic intracardiac activity and together with electrodes 3 and 5 can be used to sense the R-wave in place of external ECG electrodes for correct triggering of the defibrillation shock to the R-wave in order to avoid the induction ventricular fibrillation following a non-synchronized shock application.

Accordingly this invention has advanced the state of the art by introducing a novel method of treatment of atrial disorders resulting in atrial fibrillation which incorporates novel electrode placements, non-implantable catheter instrumentation features and the ability to continuously monitor short term atrial behavior for such purposes as post-operative monitoring of cardiac surgery. Those features of novelty embodying the nature and spirit of the invention are defined with particularity in the following claims.

I claim:

1. A method of treating atrial fibrillation of a patient's heart comprising the steps of utilizing a temporary implantable thin elongate flexible catheter body having a proximal end and a distal end, and spaced-apart first and second low impedance electrodes positioned on the catheter body with said second electrode adjacent to the distal end thereof, passing the catheter body through a path including the right side of the patient's heart and the pulmonary artery valve so that said first and second electrodes are located respectively in the right atrium and the pulmonary artery, securing the catheter body so that the second electrode is held in place in the pulmonary artery, and thereafter discharging electrical impulse energy of sufficient magnitude across the first and second electrodes to pass through blood and tissue of the heart between said electrodes and establish a field gradient therebetween for resetting fibrillating cells of atrial tissue thereby converting atrial fibrillation into sinus rhythm, and thereafter releasing and withdrawing the catheter body from the patient's heart along said path.

2. The method of claim 1 wherein said catheter body further includes an inflatable balloon proximate the distal end thereof, said method further comprising, during at least part of the step of passing the catheter body through said path, partly inflating said balloon and guiding the distal end of the catheter body through said path including the right side of the heart while maintaining said balloon partly inflated for aiding transport of the catheter body along said path under the influence of flow of the blood stream to position the balloon and the distal end of the catheter body in the pulmonary artery.

3. The method of claim 2 wherein the step of securing includes more fully inflating the balloon when disposed in the pulmonary artery for safe anchoring of the distal end of the catheter body to hold said second electrode in place in the pulmonary artery.

4. The method of claim 1 wherein said catheter body has a lumen extending longitudinally therethrough from the proximal end to the distal end thereof, said method further comprising the ancillary step of selectively withdrawing body fluids through said lumen while the distal end of the catheter body is located at a position in the pulmonary artery.

5. A method of treating atrial fibrillation which comprises the steps of:

inserting into the body of the patient a temporary catheter which includes a thin elongate flexible catheter body having a proximal end, a distal end, and a central portion between said proximal end and said distal end, said central portion including first and second spaced apart low impedance defibrillation electrodes thereon conforming in shape to said central portion to maintain a smooth continuous surface therewith, one of said first and second electrodes being located adjacent said distal end, said distal end including an inflatable balloon and said catheter body including an inflation lumen running from the proximal end into the balloon, an electrical connector at said proximal end, and first and second electrical conductors carried by the catheter body for coupling said electrical connector to respective ones of said first and second electrodes for selective electrical energization thereof;

advancing the distal end of said catheter body along a path including right atrium, right ventricle, and pulmonary artery adjacent left atrium of the patient's heart until the distal one of said electrodes is located in a desired position in the pulmonary artery adjacent the left atrium and the other of said electrodes is located in the right atrium;

selectively inflating said balloon through the inflation lumen to aid maneuvering of the catheter body in advancement along said path, and to temporarily and passively maintain the distal end of the catheter body in said desired position in the pulmonary artery; and electrically energizing said first and second electrodes with a defibrillating electrical shock applied through said first and second electrical conductors, when atrial fibrillation is detected and said electrodes are located respectively in the right atrium and in said desired position in the pulmonary artery adjacent the left atrium, to establish an electric field between said electrodes with a vector through a substantial mass of the right and left atria to terminate the atrial fibrillation.

6. The method of claim 5, wherein said catheter body includes additional electrode means in said central portion for use in pacing and sensing intracardiac activity of the patient's heart, and including the steps of sensing cardiac activity of the patient's heart to detect atrial fibrillation and termination thereof and pacing the patient's heart when necessary to maintain sinus rhythm.

7. The method of claim 5, wherein said catheter body includes an additional lumen running from the proximal end to the distal end thereof, and further including the step of taking blood samples from the patient through said additional lumen when the distal end of the catheter body is disposed in the pulmonary artery to provide additional information concerning the patient's cardiovascular condition.

8. The method of claim 5, wherein said catheter body includes an additional lumen running from the proximal end to the distal end thereof, and further including the step of measuring pressure in the pulmonary artery through said additional lumen when the distal end of the catheter body is disposed in the pulmonary artery, to provide additional information concerning the patient's cardiovascular condition.

9. A method of treating atrial fibrillation by temporary insertion of a catheter in the body of a patient, comprising the steps of:

obtaining a catheter with a thin cylindrical, flexible, elongate body having a proximal end and a distal end, and with first and second spaced apart, low impedance defibrillation electrodes carried by the catheter body and conforming to the cylindrical shape thereof to provide a smooth catheter surface; each of said first and second electrodes including a plurality of electrically interconnected, spaced apart, conductive rings of said cylindrical shape; the first electrode being located at or near the distal end of the catheter body and the second electrode being located toward the proximal end thereof and spaced apart from the first electrode, with first and second electrical conductor means carried by the catheter body from the proximal end thereof and connected to the first and second electrodes, respectively; a balloon attached adjacent the distal end of the catheter body; and a lumen extending longitudinally along the catheter body coupling the balloon to the proximal end of the catheter body for selective inflation and deflation of the balloon;

advancing the distal end of the catheter body through a path including the right atrial and ventricular chambers and into the pulmonary artery of the heart so that the second electrode is positioned in the right atrium of the patient's heart when the first electrode is positioned in the patient's pulmonary artery adjacent the left atrium;

partially inflating said balloon to facilitate advancing the distal end of the catheter body through a portion of said path in the direction of blood flow, and further inflating the balloon to anchor the distal end of the catheter body in place in the pulmonary artery when the balloon is positioned therein to maintain the first and second electrodes in said positions in the pulmonary artery and right atrium, respectively;

applying electrical energy defibrillating shock impulses at said proximal end of the catheter body to said first and second electrical conductor means to establish an electrical field between said first and second electrodes and through substantially the entire mass of the left and right atria for atrial defibrillation of the patient's heart; and when atrial defibrillation has been achieved, deflating the balloon to release the catheter body, and thereupon withdrawing the catheter body along said path and from the patient's body.

10. The method of claim 9, wherein said catheter includes additional electrodes carried by the catheter body for sensing and pacing electrical activity of the patient's heart, said method further including the ancillary steps of sensing electrical activity of the heart to detect onset and cessation of atrial fibrillation, and pacing the heart when necessary to maintain sinus rhythm.

11. A method to treat atrial fibrillation of a patient's heart using a catheter having a thin, flexible, elongate catheter body with distal and proximal ends and first and second spaced-apart defibrillation electrodes, said catheter being adapted for temporary insertion in the body of the patient, comprising the steps of:

detecting atrial fibrillation of the patient's heart;

threading the catheter through a path including right atrium, tricuspid valve, right ventricle, and pulmonary valve of the patient's heart, said catheter being sufficiently thin to be threaded through said path to place the distal end of the catheter body in the pulmonary artery without substantially impeding blood flow;

positioning the distal end of the catheter body in the pulmonary artery so that said first and second electrodes are disposed in the right atrium and the the pulmonary artery adjacent the left atrium of the patient's heart, respectively; and applying a defibrillating electrical shock waveform to said first and second electrodes to establish an electric field therebetween with an electric field vector through the left and right atria to terminate the atrial fibrillation and return the atria to normal sinus rhythm.

12. The method of claim 11, wherein the catheter has a balloon at the distal end of the catheter body and a lumen extending from the proximal end to the distal end of the catheter body for inflating and deflating the balloon, said method further including the steps of partially inflating the balloon to aid said threading of the catheter through a portion of said path under influence of blood flow along said path and placement of said electrodes respectively in the pulmonary artery and the right atrium, fully inflating the balloon for retention of the distal end of the catheter body in position in the pulmonary artery just prior to the step of applying the defibrillating electrical shock waveform, and deflating the balloon for withdrawal of the catheter body from the patient's body along said path after the step of applying the defibrillating electrical shock waveform achieves successful defibrillation.

* * * * *